United States Patent
Miyachi

(10) Patent No.: US 12,279,913 B2
(45) Date of Patent: Apr. 22, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 574 days.

(21) Appl. No.: 17/550,235

(22) Filed: Dec. 14, 2021

(65) Prior Publication Data

US 2022/0096057 A1 Mar. 31, 2022

Related U.S. Application Data

(63) Continuation of application No. PCT/JP2020/026402, filed on Jul. 6, 2020.

(30) Foreign Application Priority Data

Jul. 26, 2019 (JP) ................. 2019-137765

(51) Int. Cl.
*A61B 8/06* (2006.01)
*A61B 8/00* (2006.01)
(Continued)

(52) U.S. Cl.
CPC .............. *A61B 8/5246* (2013.01); *A61B 8/06* (2013.01); *A61B 8/145* (2013.01); *A61B 8/4472* (2013.01);
(Continued)

(58) Field of Classification Search
CPC ......... A61B 8/06; A61B 8/4472; A61B 8/585; G01S 7/52034; G01S 7/52071; G01S 15/8979; G01S 15/8988
See application file for complete search history.

(56) References Cited

U.S. PATENT DOCUMENTS

2003/0181811 A1\* 9/2003 Amemiya ............ A61B 8/4472
600/437
2010/0324418 A1\* 12/2010 El-Aklouk ............ G01S 7/5208
600/459
(Continued)

FOREIGN PATENT DOCUMENTS

JP 2012-245021 A 12/2012
JP 2013-153988 A 8/2013
(Continued)

OTHER PUBLICATIONS

International Search Report issued in PCT/JP2020/026402; mailed Sep. 1, 2020.
(Continued)

*Primary Examiner* — Boniface N Nganga
(74) *Attorney, Agent, or Firm* — Studebaker Brackett PLLC

(57) ABSTRACT

An ultrasound diagnostic apparatus includes an ultrasound probe including a transducer array and a diagnostic apparatus main body including a monitor that are wirelessly connected; and a color flow mode, the ultrasound probe includes a transmission and reception circuit that causes the transducer array to transmit an ultrasonic pulse toward a subject, and performs reception focusing processing on a reception signal output from the transducer array that has received an ultrasound echo from the subject to generate a sound ray signal, a flow image information generation unit that generates flow image information consisting of velocity data and at least one of dispersion data or power data on the basis of the sound ray signal, and a probe-side wireless communication circuit that wirelessly transmits the flow image information, and the diagnostic apparatus main body includes a main body-side wireless communication circuit that receives the flow image information wirelessly transmitted from the probe-side wireless communication circuit (Continued)

of the ultrasound probe, a color flow image generation unit that generates a color flow image on the basis of the flow image information, and a display control unit that displays the color flow image, on the monitor.

11 Claims, 6 Drawing Sheets

(51) Int. Cl.
  *A61B 8/14* (2006.01)
  *G16H 30/40* (2018.01)
  *G16H 40/67* (2018.01)
  *G16H 50/20* (2018.01)

(52) U.S. Cl.
  CPC ............ *A61B 8/4483* (2013.01); *A61B 8/463* (2013.01); *A61B 8/5223* (2013.01); *A61B 8/54* (2013.01); *G16H 30/40* (2018.01); *G16H 40/67* (2018.01); *G16H 50/20* (2018.01)

(56) References Cited

U.S. PATENT DOCUMENTS

2018/0028153 A1* 2/2018 Kuroiwa ................... A61B 8/14
2018/0368811 A1* 12/2018 Nakauchi ................. A61B 8/56

FOREIGN PATENT DOCUMENTS

| JP | 2014-008076 A | | 1/2014 | |
|---|---|---|---|---|
| JP | 2014198240 A | * | 10/2014 | ............... A61B 8/06 |
| JP | 2015-211726 A | | 11/2015 | |
| JP | 2020130728 A | * | 8/2020 | |

OTHER PUBLICATIONS

Written Opinion issued in PCT/JP2020/026402; mailed Sep. 1, 2020.

* cited by examiner

VELOCITY IMAGE DIRECTION

DIRECTIONAL POWER IMAGE DIRECTION

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2020/026402 filed on Jul. 6, 2020, which claims priority under 35 U.S.C. § 119(a) to Japanese Patent Application No. 2019-137765 filed on Jul. 26, 2019. The above application is hereby expressly incorporated by reference, in its entirety, into the present application.

BACKGROUND OF THE INVENTION

1. Field of the Invention

The present invention relates to an ultrasound diagnostic apparatus and a control method of the ultrasound diagnostic apparatus, and particularly to an ultrasound diagnostic apparatus and a control method of the ultrasound diagnostic apparatus in which an ultrasound probe and a diagnostic apparatus main body are wirelessly connected.

2. Description of the Related Art

In the related art, in the medical field, an ultrasound diagnostic apparatus using an ultrasound image has been put to practical use. In general, this type of ultrasound diagnostic apparatus comprises an ultrasound probe with a built-in transducer array, and a diagnostic apparatus main body connected to the ultrasound probe, and the ultrasound diagnostic apparatus causes the ultrasound probe to transmit an ultrasound beam toward a subject, receives an ultrasound echo from the subject by the ultrasound probe, and electrically processes a reception signal thereof in the diagnostic apparatus main body to generate an ultrasound image.

In recent years, an ultrasound diagnostic apparatus has been developed which is intended to improve operability and mobility of an ultrasound probe by wirelessly connecting the ultrasound probe and a diagnostic apparatus main body by wireless communication, as disclosed in JP2015-211726A, for example.

In such a wireless connection type ultrasound diagnostic apparatus, the analog reception signal output from the transducer array of the ultrasound probe is transmitted to the diagnostic apparatus main body by wireless communication, or a circuit for signal processing is built in the ultrasound probe and the reception signal output from the transducer array is subjected to digital processing in the ultrasound probe and transmitted to the diagnostic apparatus main body by wireless communication, and thereby an ultrasound image is generated in the diagnostic apparatus main body.

Further, in order to measure a state of a blood flow or the like of a subject, for example, in an ultrasound diagnostic apparatus disclosed in JP2014-008076A, a so-called complex baseband signal is generated on the basis of reception signals acquired by transmitting ultrasonic pulses from the transducer array to each scan line a plurality of times, a correlation calculation is performed on the generated complex baseband signal, a velocity, dispersion, and power, which are indicators of a blood flow, are calculated, and thereby a so-called color flow image is generated.

SUMMARY OF THE INVENTION

However, in a case where a state of a blood flow or the like is measured by the wireless connection type ultrasound diagnostic apparatus, since an information amount of the reception signals acquired by transmitting ultrasonic pulses from the transducer array to each scan line a plurality of times becomes large, it is difficult to transmit the reception signals from the ultrasound probe to the diagnostic apparatus main body by wireless communication.

Further, in the ultrasound probe, in a case where the complex baseband signal is generated on the basis of the reception signal output from the transducer array and the generated complex baseband signal is transmitted to the diagnostic apparatus main body by wireless communication to generate the color flow image on the diagnostic apparatus main body side, since the information amount of the complex baseband signal to be transmitted is large, it takes a long time to transmit the complex baseband signal by wireless communication, and thus, for example, it may be difficult to display the color flow image in real time on a monitor of the diagnostic apparatus main body.

The present invention has been made in order to solve such a problem in the related art, and an object thereof is to provide an ultrasound diagnostic apparatus and a control method of the ultrasound diagnostic apparatus which can smoothly display a color flow image in the diagnostic apparatus main body while the ultrasound probe and the diagnostic apparatus main body are wirelessly connected.

In order to achieve the object, an ultrasound diagnostic apparatus according to an aspect of the present invention is an ultrasound diagnostic apparatus comprising an ultrasound probe including a transducer array and a diagnostic apparatus main body including a monitor that are wirelessly connected; and a color flow mode, in which the ultrasound probe includes a transmission and reception circuit that causes the transducer array to transmit an ultrasonic pulse toward a subject, and performs reception focusing processing on a reception signal output from the transducer array that has received an ultrasound echo from the subject to generate a sound ray signal, a flow image information generation unit that generates flow image information consisting of velocity data and at least one of dispersion data or power data on the basis of the sound ray signal generated by the transmission and reception circuit, and a probe-side wireless communication circuit that wirelessly transmits the flow image information generated by the flow image information generation unit, and the diagnostic apparatus main body includes a main body-side wireless communication circuit that receives the flow image information wirelessly transmitted from the probe-side wireless communication circuit of the ultrasound probe, a color flow image generation unit that generates a color flow image on the basis of the flow image information received by the main body-side wireless communication circuit, and a display control unit that displays the color flow image generated by the color flow image generation unit, on the monitor.

The flow image information generation unit may generate the velocity data and the power data, and the color flow image generation unit may generate a velocity image as the color flow image on the basis of the velocity data and the power data that are received by the main body-side wireless communication circuit.

It is preferable that the color flow image generation unit does not generate the velocity image for a pixel in which the power data is greater than a predetermined power threshold value. Alternatively, the color flow image generation unit may not generate the velocity image for a pixel in which the power data is greater than a predetermined power threshold value and the velocity data is smaller than a predetermined velocity threshold value.

The flow image information generation unit may generate the velocity data and the power data, and the color flow image generation unit may generate a directional power image as the color flow image on the basis of the velocity data and the power data that are received by the main body-side wireless communication circuit.

Alternatively, the flow image information generation unit may generate the velocity data and the dispersion data, and the color flow image generation unit may generate a velocity dispersion image as the color flow image on the basis of the velocity data and the dispersion data that are received by the main body-side wireless communication circuit.

The ultrasound probe may include an image compression unit that image-compresses the flow image information generated by the flow image information generation unit, and the probe-side wireless communication circuit may wirelessly transmit the flow image information that is image-compressed by the image compression unit.

It is preferable that the ultrasound probe includes a B-mode image generation unit that generates a B-mode image on the basis of the sound ray signal generated by the transmission and reception circuit, the probe-side wireless communication circuit wirelessly transmits the B-mode image generated by the B-mode image generation unit and the flow image information generated by the flow image information generation unit, the main body-side wireless communication circuit receives the B-mode image and the flow image information, and the display control unit displays the B-mode image and the color flow image on the monitor.

A control method of an ultrasound diagnostic apparatus according to another aspect of the present invention is a control method of an ultrasound diagnostic apparatus that includes an ultrasound probe including a transducer array and a diagnostic apparatus main body including a monitor that are wirelessly connected, and a color flow mode, and the control method comprises, in the ultrasound probe, causing the transducer array to transmit an ultrasonic pulse toward a subject, and performing reception focusing processing on a reception signal output from the transducer array that has received an ultrasound echo from the subject to generate a sound ray signal, generating a complex baseband signal on the basis of the generated sound ray signal, generating flow image information consisting of velocity data and at least one of dispersion data or power data on the basis of the generated complex baseband signal, and wirelessly transmitting the generated flow image information to the diagnostic apparatus main body, and in the diagnostic apparatus main body, receiving the flow image information wirelessly transmitted from the ultrasound probe, generating a color flow image on the basis of the received flow image information, and displaying the generated color flow image on the monitor.

According to the present invention, the ultrasound probe includes the flow image information generation unit that generates the flow image information consisting of the velocity data and at least one of the dispersion data or the power data on the basis of the sound ray signal generated by the transmission and reception circuit, and the probe-side wireless communication circuit that wirelessly transmits the flow image information generated by the flow image information generation unit, and the diagnostic apparatus main body includes the main body-side wireless communication circuit that receives the flow image information wirelessly transmitted from the probe-side wireless communication circuit of the ultrasound probe, the color flow image generation unit that generates the color flow image on the basis of the flow image information received by the main body-side wireless communication circuit, and the display control unit that displays the color flow image generated by the color flow image generation unit, on the monitor. Therefore, it is possible to smoothly display the color flow image in the diagnostic apparatus main body while the ultrasound probe and the diagnostic apparatus main body are wirelessly connected.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
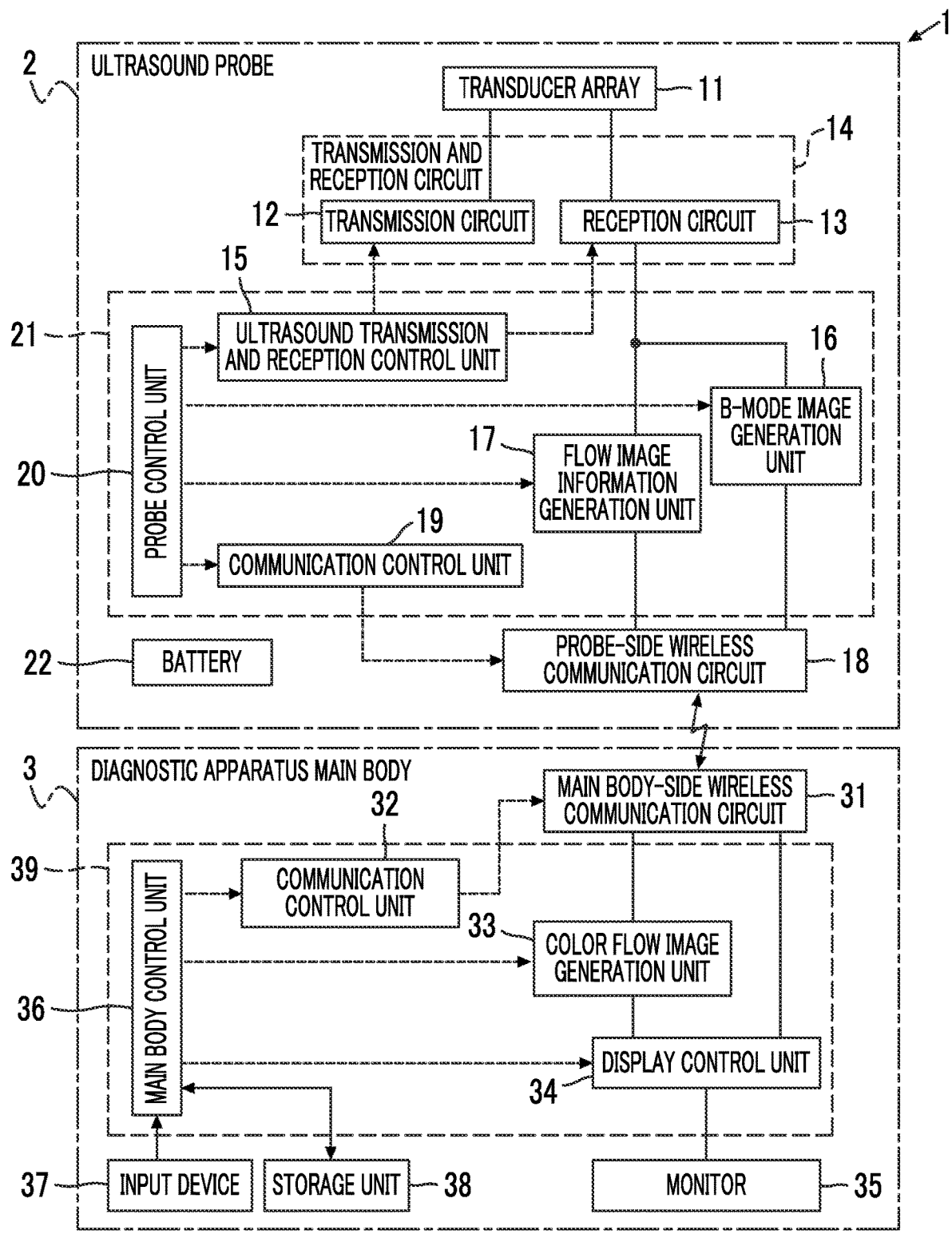
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 is an ultrasound diagnostic apparatus that has an ultrasound probe 2, and a diagnostic apparatus main body 3 wirelessly connected to the ultrasound probe 2, and comprises a color flow mode. Here, the "color flow mode" refers to a display mode in which, by so-called color flow mapping, colors are added according to the hemodynamics in a subject to be displayed in real time while being superimposed on a B-mode image.

As illustrated in FIG. 1, the ultrasound probe 2 has a transducer array 11, and a transmission circuit 12 and a reception circuit 13 are connected to the transducer array 11. The transmission circuit 12 and the reception circuit 13 constitute a transmission and reception circuit 14, and an ultrasound transmission and reception control unit 15 is connected to the transmission circuit 12 and the reception circuit 13. A B-mode image generation unit 16 and a flow image information generation unit 17 are connected in parallel to the reception circuit 13, and a probe-side wireless communication circuit 18 is connected to the B-mode image generation unit 16 and the flow image information generation unit 17.

A communication control unit 19 is connected to the probe-side wireless communication circuit 18, and a probe control unit 20 is connected to the ultrasound transmission and reception control unit 15, the B-mode image generation unit 16, the flow image information generation unit 17, and the communication control unit 19. The ultrasound transmission and reception control unit 15, the B-mode image generation unit 16, the flow image information generation unit 17, the communication control unit 19, and the probe control unit 20 constitute a probe-side processor 21. A battery 22 is built in the ultrasound probe 2.

On the other hand, the diagnostic apparatus main body 3 has a main body-side wireless communication circuit 31, and a communication control unit 32 is connected to the main body-side wireless communication circuit 31. Further, a color flow image generation unit 33 is connected to the main body-side wireless communication circuit 31, and a display control unit 34 and a monitor 35 are sequentially connected to the main body-side wireless communication circuit 31 and the color flow image generation unit 33.

A main body control unit 36 is connected to the communication control unit 32, the color flow image generation unit 33, and the display control unit 34, and an input device 37 and a storage unit 38 are connected to the main body control unit 36. Here, the main body control unit 36 and the storage unit 38 are connected so as to exchange information bidirectionally. The communication control unit 32, the color flow image generation unit 33, the display control unit 34, and the main body control unit 36 constitute a main body-side processor 39.

The transducer array 11 of the ultrasound probe 2 has a plurality of ultrasonic transducers arranged in a one-dimensional or two-dimensional manner. According to a drive signal supplied from the transmission circuit 12, each of the transducers transmits an ultrasonic wave and receives a reflected wave from the subject to output an analog reception signal. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The ultrasound transmission and reception control unit 15 controls the transmission circuit 12 and the reception circuit 13 of the transmission and reception circuit 14 to perform transmission of ultrasound beams and reception of ultrasound echoes on the basis of an inspection mode and a scanning method instructed from the probe control unit 20. Here, the inspection mode includes at least a brightness mode (B mode) and a color flow mode (CF mode), and also includes inspection modes such as a pulsed wave Doppler mode (PW mode) and a continuous wave Doppler mode (CW mode) that can be used in the ultrasound diagnostic apparatus, and the scanning method indicates, for example, any one of an electronic sector scanning method, an electronic linear scanning method, an electronic convex scanning method, or the like.

The transmission and reception circuit 14 causes the transducer array 11 to transmit the ultrasound beam toward the subject, and performs reception focusing processing on the reception signal output from the transducer array 11 that has received the ultrasound echo from the subject to generate a sound ray signal.

The transmission circuit 12 of the transmission and reception circuit 14 includes, for example, a plurality of pulse generators, and the transmission circuit 12 adjusts the amount of delay of each drive signal so that ultrasonic waves transmitted from the plurality of transducers of the transducer array 11 form an ultrasound beam on the basis of a transmission delay pattern selected according to a control signal from the ultrasound transmission and reception control unit 15, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and the ultrasound echo propagates toward the transducer array 11. The ultrasound echo propagating toward the transducer array 11 in this manner is received by each transducer constituting the transducer array 11. In this case, each transducer constituting the transducer array 11 expands and contracts by receiving the propagating ultrasound echo to generate a reception signal (electric signal), and outputs the reception signal to the reception circuit 13.

Figure 2:
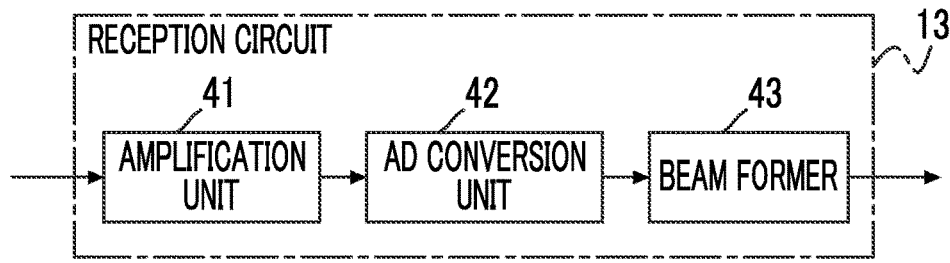
FIG. 2 is a block diagram illustrating an internal configuration of a reception circuit in the first embodiment of the present invention.

The reception circuit 13 of the transmission and reception circuit 14 processes the signal output from the transducer array 11 according to the control signal from the ultrasound transmission and reception control unit 15 to generate a sound ray signal. As illustrated in FIG. 2, the reception circuit 13 has a configuration in which an amplification unit 41, an analog digital (AD) conversion unit 42, and a beam former 43 are connected in series.

The amplification unit 41 amplifies the reception signal as the analog signal input from each transducer constituting the transducer array 11, and transmits the amplified reception signal to the AD conversion unit 42.

The AD conversion unit 42 converts the analog reception signal transmitted from the amplification unit 41 into a digital signal to acquire reception data, and sends the reception data to the beam former 43.

The beam former 43 performs so-called reception focusing processing in which addition (phasing addition) is performed by giving delays to respective pieces of the reception data according to a set sound velocity, on the basis of a reception delay pattern selected according to the control signal from the ultrasound transmission and reception control unit 15. By performing the reception focusing processing, a sound ray signal with narrowed focus of the ultrasound echo is generated.

Figure 3:
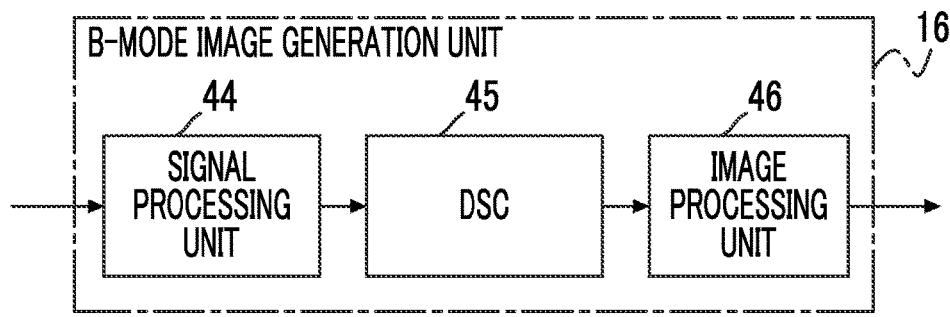
FIG. 3 is a block diagram illustrating an internal configuration of a B-mode image generation unit in the first embodiment of the present invention.

The B-mode image generation unit 16 generates a so-called B-mode image on the basis of the sound ray signal generated by the reception circuit 13 of the transmission and reception circuit 14. As illustrated in FIG. 3, the B-mode image generation unit 16 has a configuration in which a signal processing unit 44, a digital scan converter (DSC) 45, and an image processing unit 46 are sequentially connected in series.

The signal processing unit 44 generates a B-mode image signal, which is tomographic image information regarding the body tissues of the subject, by performing, on the sound ray signal generated by the reception circuit 13, correction of the attenuation due to the distance according to the depth of the reflection position of the ultrasonic wave and then performing envelope detection processing.

The DSC 45 converts (raster conversion) the B-mode image signal generated by the signal processing unit 44 into an image signal according to a normal television signal scanning method.

The image processing unit 46 performs various kinds of necessary image processing such as gradation processing on the B-mode image signal input from the DSC 45, and then outputs the B-mode image signal (B-mode image), which has been subjected to the image processing, to the probe-side wireless communication circuit 18.

Figure 4:
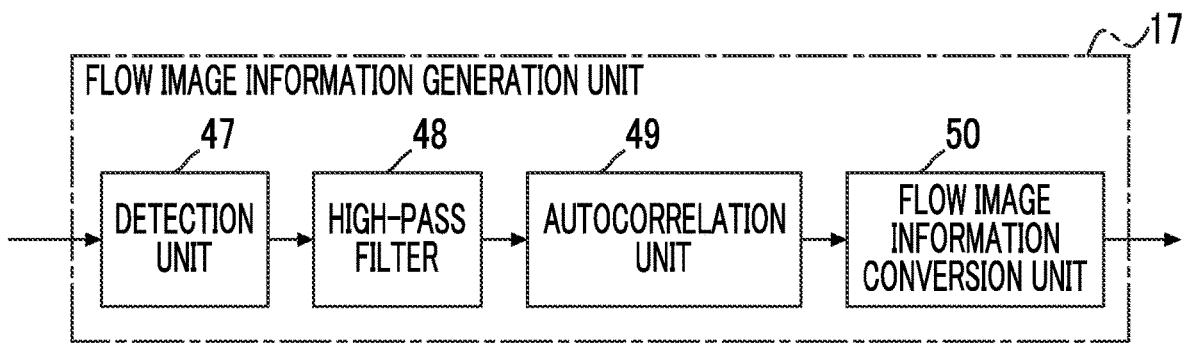
FIG. 4 is a block diagram illustrating an internal configuration of a flow image information generation unit in the first embodiment of the present invention.

The flow image information generation unit 17 generates flow image information regarding the velocity, dispersion, and power, which are indicators of hemodynamics in a circulatory system such as blood vessels and heart of the subject, on the basis of the sound ray signal generated by the reception circuit 13 of the transmission and reception circuit 14. As illustrated in FIG. 4, the flow image information generation unit 17 has a configuration in which a detection unit 47, a high-pass filter 48, an autocorrelation unit 49, and a flow image information conversion unit 50 are connected in series.

The detection unit 47 generates a so-called complex baseband signal on the basis of the sound ray signal generated by the reception circuit 13 of the transmission and reception circuit 14. More specifically, the detection unit 47 mixes the sound ray signal with a carrier signal having a reference frequency to perform quadrature detection on the sound ray signal, and converts the sound ray signal into the complex baseband signal.

The high-pass filter 48 functions as a so-called wall filter, and removes a signal of a low frequency component derived from the motion of the body tissue of the subject, which is a so-called clutter signal, from the complex baseband signal generated by the detection unit 47.

The autocorrelation unit 49 performs autocorrelation processing on the complex baseband signal from which the clutter signal is removed by the high-pass filter 48 to generate autocorrelation signals X and Y represented by Expression (1) and Expression (2).

$$X = \Sigma(I_{n-1} \cdot I^*_n + Q_{n-1} \cdot Q^*_n)/(REP-1)(n=1,2,\ldots,REP-1) \quad (1)$$

$$Y = \Sigma(I_{n-1} \cdot Q^*_n - Q_{n-1} \cdot I^*_n)/(REP-1)(n=1,2,\ldots,REP-1) \quad (2)$$

Here, $I_n$ and $Q_n$ are complex baseband signals from which the clutter signals are removed by the high-pass filter 48, and $I_n$ and $Q_n$ are signals that are 90 degrees out of phase with each other. First, $I^*_n$ represents the complex conjugate of $I_n$, and $Q^*_n$ represents the complex conjugate of $Q_n$. REP is the number of repeated transmissions of ultrasonic pulses transmitted from the transducer array 11 into the subject per scan line.

The flow image information conversion unit 50 generates flow image information consisting of power data, velocity data, and dispersion data, on the basis of the autocorrelation signals X and Y generated by the autocorrelation unit 49. For example, the flow image information conversion unit 50 converts the autocorrelation signals X and Y into power data P according to Expression (3) described below.

$$P = \Sigma(I_n \cdot I^*_n + Q_n \cdot Q^*_n)/REP(n=1,2,\ldots,REP-1) \quad (3)$$

The power data P indicates the signal intensity at each point, and is an indicator indicating the intensity of blood flow.

The flow image information conversion unit 50 can convert the autocorrelation signals X and Y into velocity data V according to Expression (4) described below.

$$V = \tan^{-1}(X, Y) \quad (4)$$

The velocity data V is an indicator indicating the direction and velocity of the blood flow at each point.

Further, the flow image information conversion unit 50 can convert the autocorrelation signals X and Y into dispersion data A according to Expression (5) described below.

$$A = 1.0 - \{(X/P)^2 + (Y/P)^2\}^{0.5} \quad (5)$$

The dispersion data A is an indicator indicating the variation in velocity with respect to the number of repeated transmissions REP of ultrasonic pulses transmitted from the transducer array 11 into the subject per scan line.

The velocity data V, dispersion data A, and power data P generated by the flow image information conversion unit 50 in this manner are converted into, for example, 8-bit data, and output to the probe-side wireless communication circuit 18, respectively.

The power data P obtained by Expression (3) can be converted into a decibel value in a case where the power data P has a large value as it is.

The velocity data V, dispersion data A, and power data P can be represented as 8-bit data by being converted into 256 integer values from 0 to 255, for example.

The flow image information conversion unit 50 can generate all the velocity data V, dispersion data A, and power data P, but can be configured to generate only the velocity data V and the power data P, or the velocity data V and the dispersion data A without necessarily generating all the velocity data V, dispersion data A, and power data P.

The probe-side wireless communication circuit 18 wirelessly transmits the B-mode image generated by the B-mode image generation unit 16 and the flow image information generated by the flow image information generation unit 17, to the diagnostic apparatus main body 3.

More specifically, the probe-side wireless communication circuit 18 includes an antenna for transmitting and receiving radio waves, modulates a carrier on the basis of the B-mode image and the flow image information to generate a transmission signal, and transmits radio waves from the antenna by supplying the transmission signal to the antenna to wirelessly transmit the B-mode image and the flow image information to the diagnostic apparatus main body 3. As the modulation method of the carrier, amplitude shift keying (ASK), phase shift keying (PSK), quadrature phase shift keying (QPSK), 16 quadrature amplitude modulation (16QAM), or the like is used.

The communication control unit 19 controls the probe-side wireless communication circuit 18 such that the B-mode image and the flow image information are transmitted with a transmission radio field intensity set by the probe control unit 20.

The probe control unit 20 controls each unit of the ultrasound probe 2 on the basis of a program and the like stored in advance.

The battery 22 is built in the ultrasound probe 2, and supplies power to each circuit of the ultrasound probe 2.

The probe-side processor 21 of the ultrasound probe 2, which has the ultrasound transmission and reception control unit 15, the B-mode image generation unit 16, the flow image information generation unit 17, the communication control unit 19, and the probe control unit 20, is configured by a central processing unit (CPU) that executes various programs and a control program for causing the CPU to execute various kinds of processing, but the probe-side processor 21 may be configured by using a field programmable gate array (FPGA), a digital signal processor (DSP), an application specific integrated circuit (ASIC), a graphics processing unit (GPU), or other integrated circuits (IC) or may be configured by a combination thereof.

The ultrasound transmission and reception control unit 15, the B-mode image generation unit 16, the flow image information generation unit 17, the communication control unit 19, and the probe control unit 20 of the probe-side processor 21 can also be configured by being integrated partially or entirely into one CPU or the like.

The main body-side wireless communication circuit 31 of the diagnostic apparatus main body 3 receives the B-mode image and the flow image information that are wirelessly transmitted from the probe-side wireless communication circuit 18 of the ultrasound probe 2.

More specifically, the main body-side wireless communication circuit 31 includes an antenna for transmitting and receiving radio waves, receives the transmission signal transmitted by the probe-side wireless communication circuit 18 of the ultrasound probe 2 via the antenna, demodulates the received transmission signal, and thereby sends the B-mode image to the display control unit 34 and the flow image information to the color flow image generation unit 33.

The color flow image generation unit 33 generates a color flow image signal (color flow image) indicating color information corresponding to the hemodynamics of the blood flow in the subject, on the basis of the flow image information received by the main body-side wireless communication circuit 31.

Figure 5:
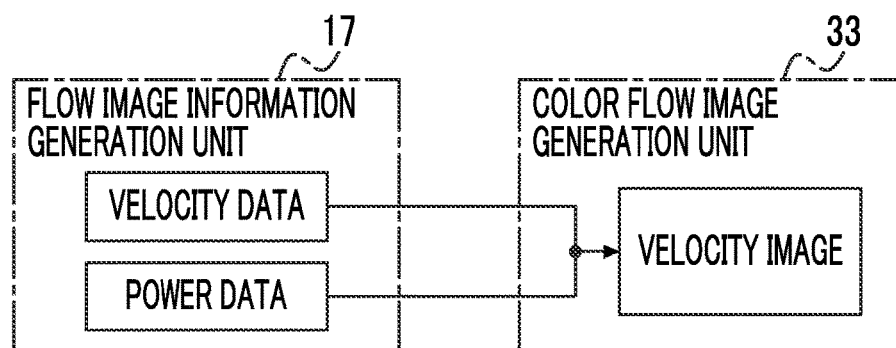
FIG. 5 is a diagram schematically illustrating a state in which a velocity image is generated by a color flow image generation unit from velocity data and power data generated by the flow image information generation unit.
Figure 6:
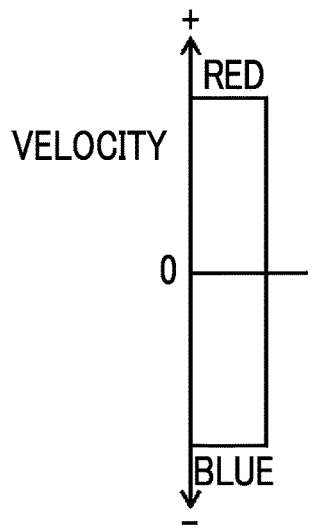
FIG. 6 is a diagram illustrating a color map of the velocity image.

As illustrated in FIG. 5, in a case where the flow image information consisting of the velocity data and the power data is generated by the flow image information generation unit 17 of the ultrasound probe 2, and is wirelessly transmitted to the main body-side wireless communication circuit 31 of the diagnostic apparatus main body 3 from the probe-side wireless communication circuit 18, the color flow image generation unit 33 can generate a velocity image as the color flow image by using the velocity data while referring to the power data. As illustrated in FIG. 6, in the velocity image, on the basis of the velocity data at each point, for each pixel, the blood flow in a direction approaching the ultrasound probe 2 is illustrated in red and the blood flow in a direction away from the ultrasound probe 2 is illustrated in blue, and the velocity of the blood flow is represented by the brightness thereof. Therefore, it is possible to intuitively grasp the distribution of the blood flow velocity.

In this case, the power data illustrates the signal intensity at each point, and for example, the blood in the blood vessel and the vascular wall generally have different values of power data. Specifically, it is known that the power data in the vascular wall is larger than the power data for the blood. For a pixel in which the power data is greater than a predetermined power threshold value, the color flow image generation unit 33 determines that the power data corresponds to the tissue such as a vascular wall instead of the blood, and thereby does not generate the velocity image.

Further, since the blood flow in a relatively large blood vessel is generally fast even in a case where the power is small, for a pixel in which the power data is greater than the predetermined power threshold value and the velocity data is smaller than a predetermined velocity threshold value, the color flow image generation unit 33 determines that the power data corresponds to the tissue such as a vascular wall, and thereby does not generate the velocity image.

Figure 7:
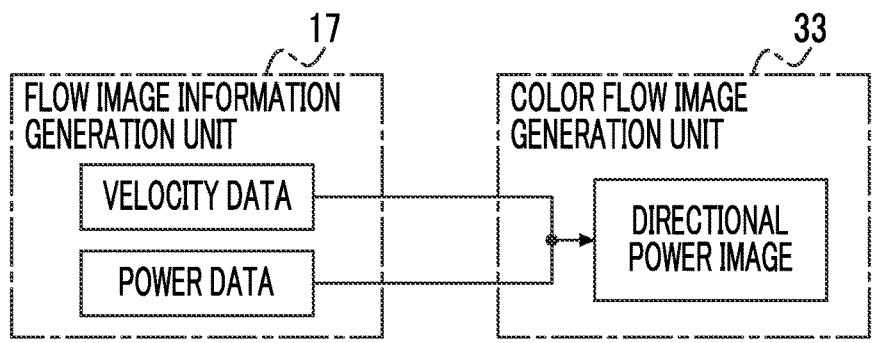
FIG. 7 is a diagram schematically illustrating a state in which a directional power image is generated by the color flow image generation unit from the velocity data and the power data generated by the flow image information generation unit.
Figure 8:
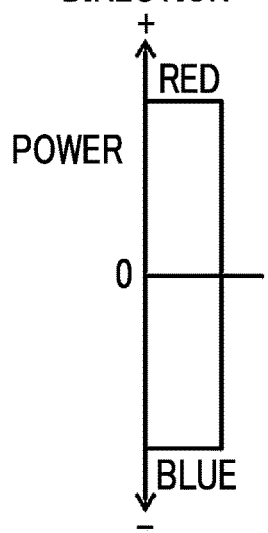
FIG. 8 is a diagram illustrating a color map of the directional power image.

Further, as illustrated in FIG. 7, in a case where the flow image information consisting of the velocity data and the power data is generated by the flow image information generation unit 17 of the ultrasound probe 2, and is wirelessly transmitted to the main body-side wireless communication circuit 31 of the diagnostic apparatus main body 3 from the probe-side wireless communication circuit 18, the color flow image generation unit 33 can generate a directional power image as the color flow image by using the velocity data and the power data. As illustrated in FIG. 8, in the directional power image, on the basis of the velocity data at each point, for each pixel, the power for the blood flow in a direction approaching the ultrasound probe 2 is illustrated in red and the power for the blood flow in a direction away from the ultrasound probe 2 is illustrated in blue, and the magnitude of the power is represented by the brightness thereof. Therefore, it is possible to intuitively grasp a blood flow direction together with the distribution of the power.

Figure 9:
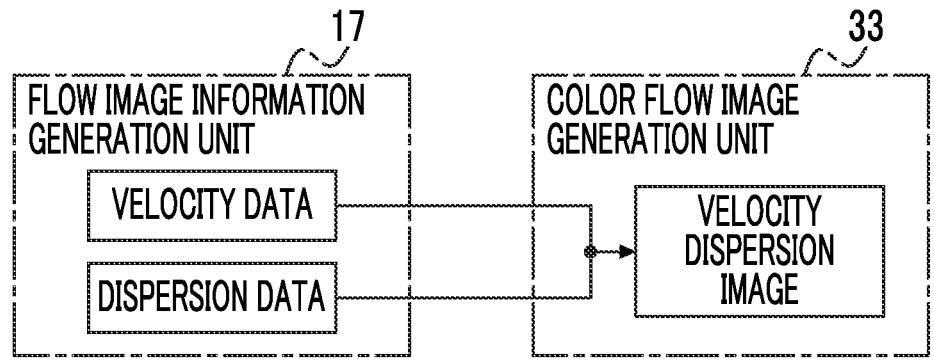
FIG. 9 is a diagram schematically illustrating a state in which a velocity dispersion image is generated by the color flow image generation unit from the velocity data and dispersion data generated by the flow image information generation unit.
Figure 10:
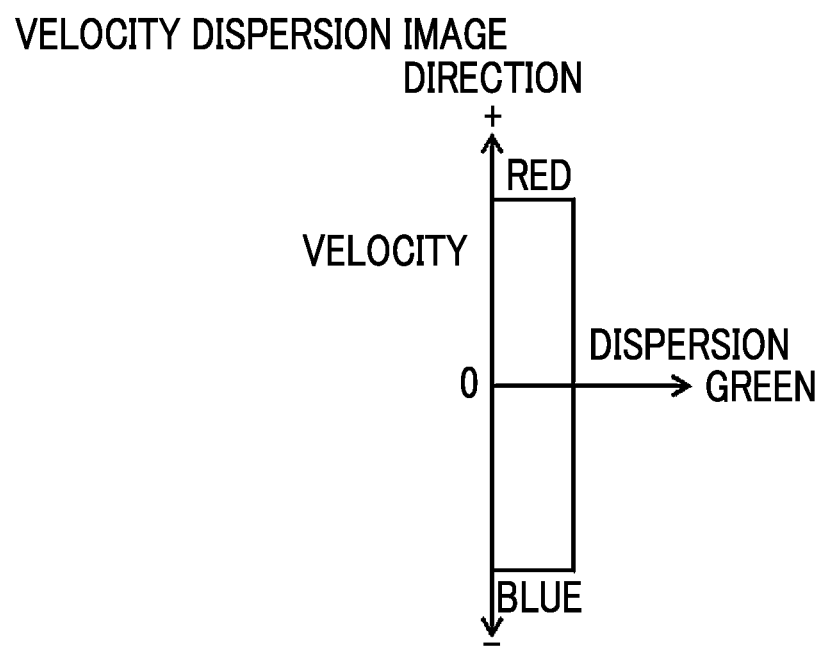
FIG. 10 is a diagram illustrating a color map of the velocity dispersion image.

As illustrated in FIG. 9, in a case where the flow image information consisting of the velocity data and the dispersion data is generated by the flow image information generation unit 17 of the ultrasound probe 2, and is wirelessly transmitted to the main body-side wireless communication circuit 31 of the diagnostic apparatus main body 3 from the probe-side wireless communication circuit 18, the color flow image generation unit 33 can generate a velocity dispersion image as the color flow image by using the velocity data and the dispersion data. The velocity dispersion image is an image in which a value of the dispersion data is added to the velocity image. That is, as illustrated in FIG. 10, in the velocity dispersion image, on the basis of the velocity data at each point, for each pixel, for example, the blood flow in a direction approaching the ultrasound probe 2 is illustrated in red and the blood flow in a direction away from the ultrasound probe 2 is illustrated in blue, the velocity of the blood flow is represented by the brightness thereof, and a component of, for example, a green color is added according to the value of the dispersion data at each point. Therefore, it is possible to intuitively grasp the distribution of the blood flow velocity and the degree of variation in the blood flow velocity.

Further, the flow image information consisting of the velocity data, the dispersion data, and the power data is generated by the flow image information generation unit 17 of the ultrasound probe 2, and is wirelessly transmitted to the main body-side wireless communication circuit 31 of the diagnostic apparatus main body 3 from the probe-side wireless communication circuit 18. In this case, the color flow image generation unit 33 can select and generate any color flow image among the velocity image, the directional power image, and the velocity dispersion image, on the basis of an operator's operation.

For example, in a case where the flow image information consisting of the velocity data and the power data is generated by the flow image information generation unit 17 of the ultrasound probe 2, and is wirelessly transmitted to the main body-side wireless communication circuit 31 of the diagnostic apparatus main body 3 from the probe-side wireless communication circuit 18, the color flow image generation unit 33 can generate not only the velocity image or the directional power image as illustrated in FIG. 5 or FIG. 7, but also a so-called power image indicating only the distribution of the power without adding the blood flow direction on the basis of the power data.

Similarly, in a case where the flow image information consisting of the velocity data and the dispersion data is generated by the flow image information generation unit 17 of the ultrasound probe 2, and is wirelessly transmitted to the main body-side wireless communication circuit 31 of the diagnostic apparatus main body 3 from the probe-side wireless communication circuit 18, the color flow image generation unit 33 can generate not only the velocity dispersion image as illustrated in FIG. 9, but also the velocity image indicating only the distribution of the velocity without adding the dispersion on the basis of the velocity data.

The display control unit 34 displays the color flow image generated by the color flow image generation unit 33 as a display image on the monitor 35. Specifically, in the first embodiment, the display control unit 34 displays the color flow image generated by the color flow image generation unit 33 and the B-mode image received by the main body-side wireless communication circuit 31 in a superimposed manner, as the display image on the monitor 35. The display control unit 34 may perform any image processing on the display image to display the display image subjected to the image processing, on the monitor 35.

The monitor 35 is for displaying the color flow image generated by the color flow image generation unit 33, as the display image under the control of the display control unit 34, and includes a display device such as a liquid crystal display (LCD), or an organic electroluminescence (EL) display. In the case of the first embodiment, the monitor 35 displays the color flow image generated by the color flow image generation unit 33 and the B-mode image received by the main body-side wireless communication circuit 31 in a superimposed manner, as the display image.

The communication control unit 32 controls the main body-side wireless communication circuit 31 such that the reception of the transmission signal transmitted from the probe-side wireless communication circuit 18 of the ultrasound probe 2 is performed.

The main body control unit 36 controls each unit of the diagnostic apparatus main body 3 on the basis of a program stored in advance in the storage unit 38 or the like and the operator's input operation through the input device 37.

The input device 37 is for the operator to perform an input operation, and can be configured to comprise a keyboard, a mouse, a trackball, a touchpad, a touch panel, and the like. A touch sensor can be combined with the monitor 35, and the touch sensor can be used as the input device 37. The input device 37 by using such a touch sensor is extremely effective for outdoor diagnosis during emergency treatment or the like.

The storage unit 38 stores a control program and the like of the diagnostic apparatus main body 3, and recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used as the storage unit 38.

The main body-side processor 39 of the diagnostic apparatus main body 3, which has the communication control unit 32, the color flow image generation unit 33, the display control unit 34, and the main body control unit 36 is configured by a CPU and a control program causing the CPU to execute various kinds of processing, but may be configured by using FPGA, DSP, ASIC, GPU, or other ICs, or may be configured by a combination thereof.

In addition, the communication control unit 32, the color flow image generation unit 33, the display control unit 34, and the main body control unit 36 of the main body-side processor 39 can also be configured by being integrated partially or entirely into one CPU or the like.

Figure 11:
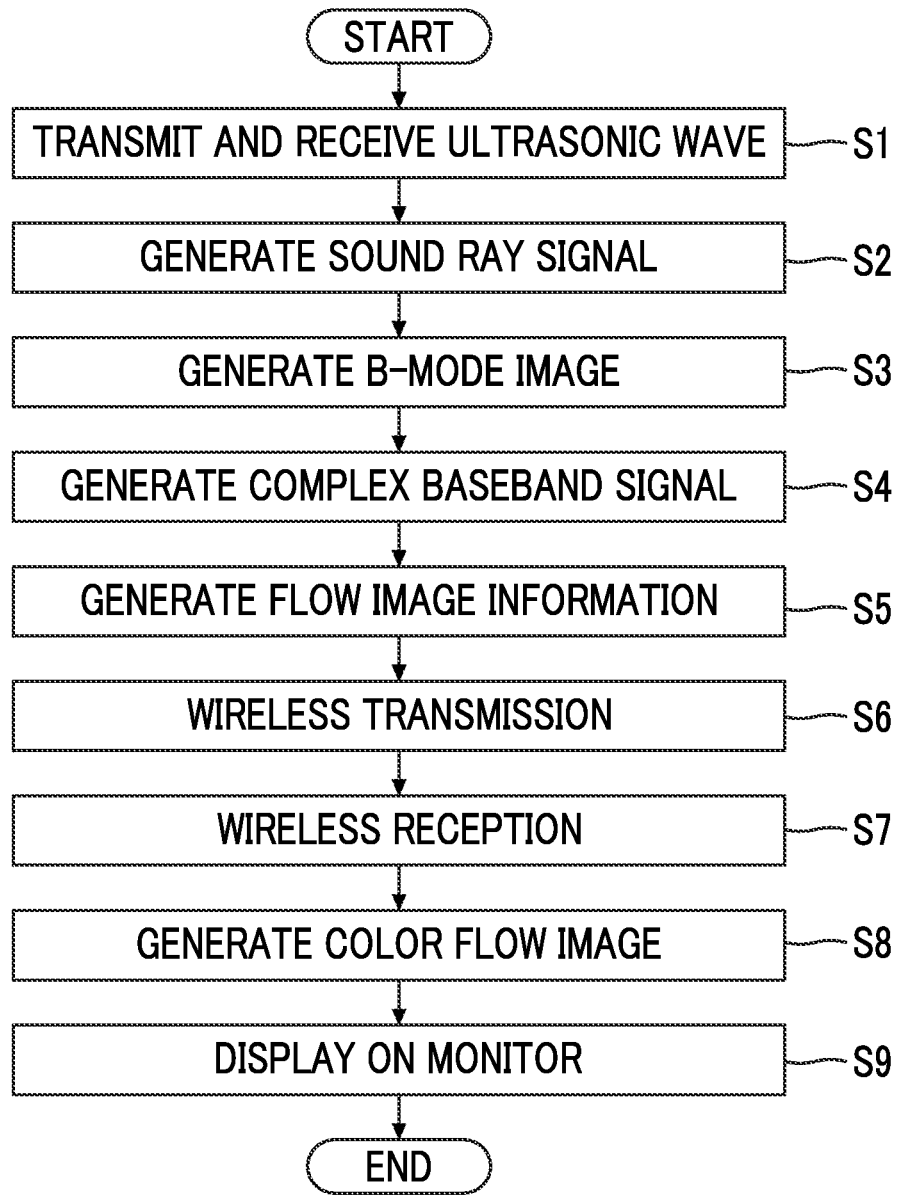
FIG. 11 is a flowchart illustrating an operation of the ultrasound diagnostic apparatus according to the first embodiment of the present invention.

Next, the operation of the ultrasound diagnostic apparatus 1 consisting of the ultrasound probe 2 and the diagnostic apparatus main body 3 will be described with reference to the flowchart of FIG. 11.

In the ultrasound probe 2, under the control of the ultrasound transmission and reception control unit 15, the ultrasound beam is transmitted into the subject from the plurality of transducers of the transducer array 11 according to the drive signal of the transmission circuit 12 of the transmission and reception circuit 14. The ultrasound echo by the subject is received by the plurality of transducers of the transducer array 11, the reception signal as the analog signal is output from the plurality of transducers to the reception circuit 13, is amplified in the amplification unit 41, and is subjected to the AD conversion in the AD conversion unit 42, and thereby the reception data is acquired (Step S1). By performing the reception focusing processing on the reception data by the beam former 43, a sound ray signal is generated (Step S2).

The sound ray signal generated by the beam former 43 of the reception circuit 13 is input to the B-mode image generation unit 16, and the B-mode image is generated by the B-mode image generation unit 16 (Step S3). In this case, the signal processing unit 44 of the B-mode image generation unit 16 performs the correction of the attenuation due to the distance according to the depth of the reflection position of the ultrasonic wave and the envelope detection processing, the DSC 45 performs the conversion into the image signal according to a normal television signal scanning method, and the image processing unit 46 performs various kinds of necessary image processing such as gradation processing.

The sound ray signal generated by the beam former 43 of the reception circuit 13 is also input to the flow image information generation unit 17.

The detection unit 47 of the flow image information generation unit 17 mixes the sound ray signal with the carrier signal having a reference frequency to perform quadrature detection on the sound ray signal, and generates a complex baseband signal (Step S4).

The complex baseband signal generated in this manner is subjected to the removal of the low frequency component derived from the motion of the body tissue of the subject, which is a so-called clutter signal, by the high-pass filter 48, and then the autocorrelation signals X and Y represented by Expression (1) and Expression (2) are generated by the autocorrelation unit 49.

Further, the flow image information is generated by the flow image information conversion unit 50 on the basis of the autocorrelation signals X and Y (Step S5).

The flow image information conversion unit 50 can generate at least one of the velocity data V represented by Expression (4), the dispersion data A represented by Expression (5), or the power data P represented by Expression (3), as the flow image information, from the autocorrelation signals X and Y. That is, all the velocity data V, the dispersion data A, and the power data P, the velocity data V and power data P or the velocity data V and dispersion data A are generated by the flow image information conversion unit 50.

In general, the signal intensity of the clutter signal may be, for example, 300 times to 1000 times stronger than the signal intensity of the blood flow signal derived from the blood flow among the signals included in the complex baseband signal. Therefore, in a state where the complex baseband signal includes both the clutter signal and the blood flow signal, if it is assumed that the complex baseband signal is converted into the flow image information, it is considered that the blood flow signal is significantly deteriorated due to the difference in signal intensity between the clutter signal and the blood flow signal. In the ultrasound diagnostic apparatus 1 according to the first embodiment, since the high-pass filter 48 of the flow image information generation unit 17 removes the clutter signal from the complex baseband signal generated by the detection unit 47, it is possible to prevent the blood flow signal from being deteriorated in the process of converting the complex baseband signal into the flow image information.

The flow image information generated by the flow image information conversion unit 50 and the B-mode image generated by the B-mode image generation unit 16 are wirelessly transmitted from the probe-side wireless communication circuit 18 to the diagnostic apparatus main body 3 under the control of the communication control unit 19 (Step S6).

Here, in a case where the complex baseband signal generated by the detection unit 47 of the flow image information generation unit 17 is transmitted to the diagnostic apparatus main body 3 by wireless communication as it is, and the color flow image is generated on the diagnostic apparatus main body 3 side, since the information amount of the complex baseband signal to be transmitted is large, it takes a long time to transmit the complex baseband signal by wireless communication, and it becomes difficult to wirelessly transmit the complex baseband signal, for example, data loss occurs during wireless transmission, in particular, in a case where the wireless communication state is unstable.

In the ultrasound diagnostic apparatus 1 of the first embodiment, the complex baseband signal generated by the detection unit 47 of the flow image information generation unit 17 is subjected to the removal of the clutter signal by the high-pass filter 48, and is input to the autocorrelation unit 49 so that the autocorrelation signals X and Y are generated, and the flow image information is generated by the flow image information conversion unit 50 on the basis of the autocorrelation signals X and Y.

Therefore, the flow image information of which the information amount is reduced as compared with the complex baseband signal generated by the detection unit 47 can be wirelessly transmitted from the probe-side wireless communication circuit 18 to the diagnostic apparatus main body 3, and in the diagnostic apparatus main body 3, the color flow image can be smoothly displayed on the monitor 35.

In this manner, the flow image information wirelessly transmitted from the probe-side wireless communication circuit 18 of the ultrasound probe 2 is received by the main body-side wireless communication circuit 31 of the diagnostic apparatus main body 3 (Step S7), and is sent to the color flow image generation unit 33.

The color flow image generation unit 33 generates the color flow image on the basis of the flow image information received by the main body-side wireless communication circuit 31 (Step S8).

For example, in a case where the flow image information consisting of the velocity data V and the power data P is generated by the flow image information generation unit 17 of the ultrasound probe 2, and is wirelessly transmitted to the main body-side wireless communication circuit 31 of the diagnostic apparatus main body 3 from the probe-side wireless communication circuit 18, the color flow image generation unit 33 can generate a velocity image as the color flow image by using the velocity data while referring to the power data.

The color flow image generated by the color flow image generation unit 33 and the B-mode image generated by the B-mode image generation unit 16 of the ultrasound probe 2 are sent to the display control unit 34.

The display control unit 34 performs predetermined processing on the color flow image generated by the color flow image generation unit 33 and the B-mode image sent from the main body-side wireless communication circuit 31 to display the images on the monitor 35 under the control of the main body control unit 36 (Step S9).

Specifically, the color flow image generated by the color flow image generation unit 33 and the B-mode image received by the main body-side wireless communication circuit 31 are displayed on the monitor 35 in a superimposed manner.

As illustrated in FIG. 5, in a case where the flow image information consisting of the velocity data V and the power data P is generated by the flow image information generation unit 17 of the ultrasound probe 2, and is wirelessly transmitted to the main body-side wireless communication circuit 31 of the diagnostic apparatus main body 3 from the probe-side wireless communication circuit 18, the color flow image generation unit 33 can generate a velocity image as the color flow image by using the velocity data V while referring to the power data P, and display the velocity image on the monitor 35 such that the velocity image is superimposed on the B-mode image. Thereby, it is possible for the operator to intuitively grasp the distribution of the blood flow velocity.

As illustrated in FIG. 7, in a case where the flow image information consisting of the velocity data V and the power data P is generated by the flow image information generation unit 17 of the ultrasound probe 2, and is wirelessly transmitted to the main body-side wireless communication circuit 31 of the diagnostic apparatus main body 3 from the probe-side wireless communication circuit 18, the color flow image generation unit 33 can generate a directional power image as the color flow image by using the velocity data V and the power data P, and display the directional power image on the monitor 35 such that the directional power image is superimposed on the B-mode image. Thereby, it is possible for the operator to intuitively grasp the blood flow direction together with the distribution of power.

As illustrated in FIG. 9, in a case where the flow image information consisting of the velocity data V and the dispersion data A is generated by the flow image information generation unit 17 of the ultrasound probe 2, and is wirelessly transmitted to the main body-side wireless communication circuit 31 of the diagnostic apparatus main body 3 from the probe-side wireless communication circuit 18, the color flow image generation unit 33 can generate a velocity dispersion image as the color flow image by using the velocity data V and the dispersion data A, and display the velocity dispersion image on the monitor 35 such that the velocity dispersion image is superimposed on the B-mode image. Thereby, it is possible for the operator to intuitively grasp the distribution of the blood flow velocity and the degree of variation in the blood flow velocity.

Further, the flow image information including all the velocity data V, the dispersion data A, and the power data P can be generated by the flow image information generation unit 17 of the ultrasound probe 2, and be wirelessly transmitted to the main body-side wireless communication circuit 31 of the diagnostic apparatus main body 3 from the probe-side wireless communication circuit 18. In this case, any color flow image among the velocity image, the directional power image, and the velocity dispersion image can be generated by the operator's operation through the input device 37, and the color flow image can be displayed on the monitor 35 such that the color flow image is superimposed on the B-mode image.

In the ultrasound diagnostic apparatus 1 illustrated in FIG. 1, the reception circuit 13 of the transmission and reception circuit 14 of the ultrasound probe 2 has the beam former 43 together with the amplification unit 41 and the AD conversion unit 42, but the beam former 43 may be disposed between the reception circuit 13, and the B-mode image generation unit 16 and the flow image information generation unit 17, instead of being disposed inside the reception circuit 13. In this case, the beam former 43 can constitute the probe-side processor 21.

The B-mode image generation unit 16 of the ultrasound probe 2 has the signal processing unit 44, the DSC 45, and the image processing unit 46, but among theses, the DSC 45 and the image processing unit 46 may be disposed between the main body-side wireless communication circuit 31 and the display control unit 34 of the diagnostic apparatus main body 3, instead of being disposed inside the B-mode image generation unit 16.

In this case, the B-mode image signal generated by the envelope detection processing in the signal processing unit 44 of the B-mode image generation unit 16 is wirelessly transmitted from the probe-side wireless communication circuit 18, the B-mode image signal received by the main body-side wireless communication circuit 31 of the diagnostic apparatus main body 3 is subjected to the conversion into the image signal by the DSC 45 and the image processing by the image processing unit 46, and the B-mode image signal (B-mode image) subjected to the image processing is sent to the display control unit 34. The DSC 45 and the image processing unit 46 disposed in the diagnostic apparatus main body 3 can constitute the main body-side processor 39.

Second Embodiment

In the first embodiment, the flow image information generated by the flow image information generation unit 17 of the ultrasound probe 2 is wirelessly transmitted to the diagnostic apparatus main body 3 from the probe-side wireless communication circuit 18, but the flow image information can be wirelessly transmitted to the diagnostic apparatus main body 3 from the probe-side wireless communication circuit 18 in a state of being image-compressed.

Figure 12:
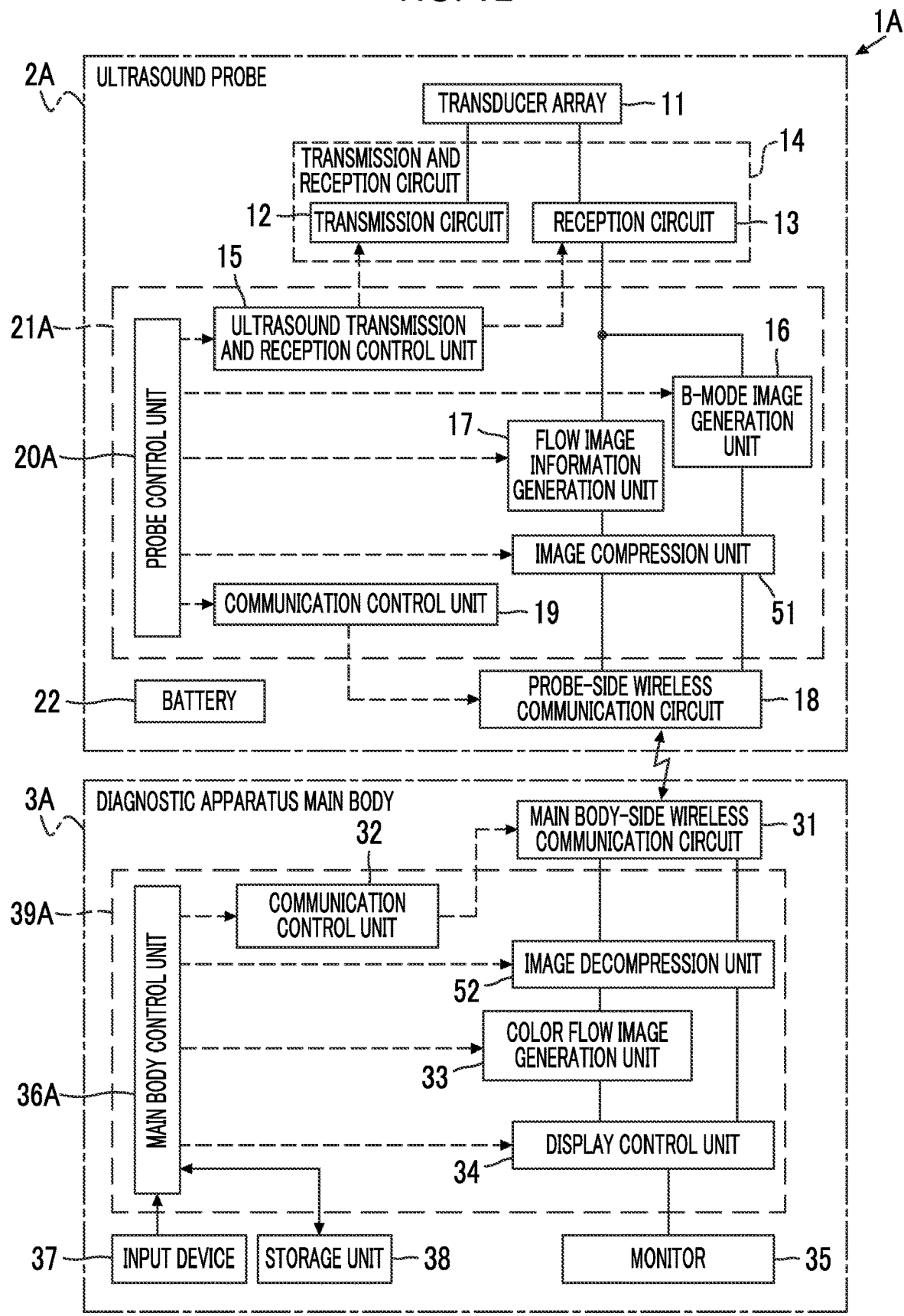
FIG. 12 is a block diagram illustrating a configuration of an ultrasound diagnostic apparatus according to a second embodiment of the present invention.

FIG. 12 illustrates a configuration of an ultrasound diagnostic apparatus 1A according to a second embodiment of the present invention. The ultrasound diagnostic apparatus 1A is obtained by comprising an ultrasound probe 2A instead of the ultrasound probe 2 and comprising a diagnostic apparatus main body 3A instead of the diagnostic apparatus main body 3 in the ultrasound diagnostic apparatus 1 of the first embodiment illustrated in FIG. 1. The ultrasound probe 2A is obtained by adding an image compression unit 51 to the ultrasound probe 2 in the first embodiment, using a probe control unit 20A instead of the probe control unit 20, and using a probe-side processor 21A instead of the probe-side processor 21. The diagnostic apparatus main body 3A is obtained by adding an image decompression unit 52 to the diagnostic apparatus main body 3 in the first embodiment, using a main body control unit 36A instead of the main body control unit 36, and using a main body-side processor 39A instead of the main body-side processor 39.

In the ultrasound probe 2A, the image compression unit 51 is connected to the flow image information generation unit 17 and the B-mode image generation unit 16, and the probe-side wireless communication circuit 18 is connected to the image compression unit 51.

In the diagnostic apparatus main body 3A, the communication control unit 32 and the image decompression unit 52 are connected to the main body-side wireless communication circuit 31, and the color flow image generation unit 33 and the display control unit 34 are connected to the image decompression unit 52.

The image compression unit 51 of the ultrasound probe 2A image-compresses the flow image information generated by the flow image information generation unit 17 into a format such as so-called Joint Photographic Experts Group (JPEG). Thereby, it is possible to further reduce the information amount of the flow image information consisting of the velocity data V and at least one of the dispersion data A or the power data P. Further, the image compression unit 51 also image-compresses the B-mode image generated by the B-mode image generation unit 16.

The image compression unit 51 can image-compress the velocity data V and the power data P at a higher compression ratio than the dispersion data A. This is because the velocity data V and the power data P include less high frequency components and more low frequency components than the dispersion data A, so that the deterioration of the data is small even in a case where the compression ratio of the image compression is increased.

On the contrary, since the B-mode image generally includes a lot of high frequency components, it is desirable to keep the compression ratio low for the purpose of preventing the deterioration of the image, in a case where the B-mode image generated by the B-mode image generation unit 16 is image-compressed by the image compression unit 51.

The probe-side wireless communication circuit 18 of the ultrasound probe 2A wirelessly transmits the flow image information and the B-mode image, which are image-compressed by the image compression unit 51, to the diagnostic apparatus main body 3A under the control of the communication control unit 19.

The main body-side wireless communication circuit 31 of the diagnostic apparatus main body 3A receives the flow image information and the B-mode image wirelessly transmitted by the probe-side wireless communication circuit 18 of the ultrasound probe 2A, and sends the received flow image information and B-mode image to the image decompression unit 52.

The image decompression unit 52 decompresses the flow image information and the B-mode image that are sent from the main body-side wireless communication circuit 31, into a format before the image compression by the image compression unit 51. That is, the image decompression unit 52 decompresses the flow image information sent from the main body-side wireless communication circuit 31 into the same format as the flow image information immediately after being generated by the flow image information generation unit 17 of the ultrasound probe 2A, and decompresses the B-mode image sent from the main body-side wireless communication circuit 31 into the same format as the B-mode image immediately after being generated by the B-mode image generation unit 16. The decompressed flow image information is sent to the color flow image generation unit 33, and the decompressed B-mode image is sent to the display control unit 34.

The color flow image generation unit 33 generates the color flow image on the basis of the flow image information decompressed by image decompression unit 52.

The display control unit 34 performs predetermined processing on the color flow image generated by the color flow image generation unit 33 and the B-mode image sent from the image decompression unit 52 to display the color flow image and the B-mode image on the monitor 35.

As described above, with the ultrasound diagnostic apparatus 1A according to the second embodiment of the present invention, the flow image information generated by the flow image information generation unit 17 is image-compressed by the image compression unit 51, and therefore, it is possible to further reduce the information amount of the flow image information. Further, the B-mode image generated by the B-mode image generation unit 16 is also compressed by the image compression unit 51, and therefore, it is possible to reduce the information amount of the B-mode image. Therefore, even in an environment in which the wireless communication state is not favorable, the color flow image can be smoothly displayed in the diagnostic apparatus main body 3A.

EXPLANATION OF REFERENCES 1, 1A: ultrasound diagnostic apparatus
2, 2A: ultrasound probe
3, 3A: diagnostic apparatus main body
11: transducer array
12: transmission circuit
13: reception circuit
14: transmission and reception circuit
15: ultrasound transmission and reception control unit
16: B-mode image generation unit
17: flow image information generation unit
18: probe-side wireless communication circuit
19, 32: communication control unit
20, 20A: probe control unit
21, 21A: probe-side processor
22: battery
31: main body-side wireless communication circuit
33: color flow image generation unit
34: display control unit
35: monitor
36, 36A: main body control unit
37: input device
38: storage unit
39, 39A: main body-side processor
41: amplification unit
42: AD conversion unit
43: beam former
44: signal processing unit
45: DSC
46: image processing unit
47: detection unit
48: high-pass filter
49: autocorrelation unit
50: flow image information conversion unit
51: image compression unit
52: image decompression unit

What is claimed is:
1. An ultrasound diagnostic apparatus comprising:
an ultrasound probe including a transducer array and a diagnostic apparatus main body including a monitor that are wirelessly connected; and a color flow mode,
wherein the ultrasound probe includes
a transmission and reception circuit that causes the transducer array to transmit an ultrasonic pulse toward a subject, and performs reception focusing processing on a reception signal output from the transducer array that has received an ultrasound echo from the subject to generate a sound ray signal,
a probe-side processor that generates a B-mode image on the basis of the sound ray signal generated by the transmission and reception circuit and generates flow image information not imaged consisting of velocity data and at least one of dispersion data or power data on the basis of the sound ray signal generated by the transmission and reception circuit, and
a probe-side wireless communication circuit that wirelessly transmits the B-mode image and the flow image information generated by the probe-side processor, and
the diagnostic apparatus main body includes
a main body-side wireless communication circuit that receives the B-mode image and the flow image information wirelessly transmitted from the probe-side wireless communication circuit of the ultrasound probe, and
a main body-side processor that displays the B-mode image on the monitor and generates a color flow image on the basis of the flow image information received by the main body-side wireless communication circuit and displays the color flow image generated on the monitor,
wherein the probe-side processor is configured to
generate a complex baseband signal on the basis of the sound ray signal,
remove a clutter signal from the complex baseband signal,
perform autocorrelation processing on the complex baseband signal from which the clutter signal is removed to generate autocorrelation signals, and
generate the flow image information on the basis of the autocorrelation signals,
wherein the flow image information generated by the probe-side processor is wirelessly transmitted by the probe-side wireless communication circuit of the ultrasound probe to the diagnostic apparatus main body.

2. The ultrasound diagnostic apparatus according to claim 1,
wherein the probe-side processor generates the velocity data and the power data, and the main body-side processor generates a velocity image as the color flow image on the basis of the velocity data and the power data that are received by the main body-side wireless communication circuit.

3. The ultrasound diagnostic apparatus according to claim 2,
wherein the main body-side processor does not generate the velocity image for a pixel in which the power data is greater than a predetermined power threshold value.

4. The ultrasound diagnostic apparatus according to claim 2,
wherein the main body-side processor does not generate the velocity image for a pixel in which the power data is greater than a predetermined power threshold value and the velocity data is smaller than a predetermined velocity threshold value.

5. The ultrasound diagnostic apparatus according to claim 2,
wherein the probe-side processor image-compresses the flow image information, and
the probe-side wireless communication circuit wirelessly transmits the flow image information that is image-compressed by the probe-side processor.

6. The ultrasound diagnostic apparatus according to claim 1,
wherein the probe-side processor generates the velocity data and the power data, and
the main body-side processor generates a directional power image as the color flow image on the basis of the velocity data and the power data that are received by the main body-side wireless communication circuit.

7. The ultrasound diagnostic apparatus according to claim 6,
wherein the probe-side processor image-compresses the flow image information, and
the probe-side wireless communication circuit wirelessly transmits the flow image information that is image-compressed by the probe-side processor.

8. The ultrasound diagnostic apparatus according to claim 1,
wherein the probe-side processor generates the velocity data and the dispersion data, and
the main body-side processor generates a velocity dispersion image as the color flow image on the basis of the velocity data and the dispersion data that are received by the main body-side wireless communication circuit.

9. The ultrasound diagnostic apparatus according to claim 8,
wherein the probe-side processor image-compresses the flow image information, and
the probe-side wireless communication circuit wirelessly transmits the flow image information that is image-compressed by the probe-side processor.

10. The ultrasound diagnostic apparatus according to claim 1,
wherein the probe-side processor image-compresses the flow image information, and
the probe-side wireless communication circuit wirelessly transmits the flow image information that is image-compressed by the probe-side processor.

11. A control method of an ultrasound diagnostic apparatus that includes an ultrasound probe including a transducer array and a diagnostic apparatus main body including a monitor that are wirelessly connected, and a color flow mode, the control method comprising:
in the ultrasound probe,
causing the transducer array to transmit an ultrasonic pulse toward a subject, and performing reception focusing processing on a reception signal output from the transducer array that has received an ultrasound echo from the subject to generate a sound ray signal,
generating a B-mode image on the basis of the generated sound ray signal,
generating a complex baseband signal on the basis of the generated sound ray signal,
removing a clutter signal from the complex baseband signal,
performing autocorrelation processing on the complex baseband signal from which the clutter signal is removed to generate autocorrelation signals,
generating flow image information not imaged consisting of velocity data and at least one of dispersion data or power data on the basis of the generated autocorrelation signals, and
wirelessly transmitting the generated B-mode image and the generated flow image information to the diagnostic apparatus main body, and
in the diagnostic apparatus main body,
receiving the B-mode image and the flow image information wirelessly transmitted from the ultrasound probe,
generating a color flow image on the basis of the received flow image information, and
displaying the received B-mode image and the generated color flow image on the monitor.

* * * * *